United States Patent [19]

Vogel

[11] 3,939,185
[45] Feb. 17, 1976

[54] PROCESS FOR THE PREPARATION OF 1-NITRO-ANTHRAQUINONE WHICH IS PRACTICALLY FREE OF 1,5-DINITRO-ANTHRAQUINONE

[75] Inventor: Axel Vogel, Cologne, Germany

[73] Assignee: Bayer Aktiengesellschaft, Leverkusen, Germany

[22] Filed: Nov. 30, 1973

[21] Appl. No.: 420,370

[30] Foreign Application Priority Data
Dec. 2, 1972    Germany............................ 2259074

[52] U.S. Cl. ................................................ 260/369
[51] Int. Cl.² ........................................ C07C 79/37
[58] Field of Search ..................................... 260/369

[56] References Cited
UNITED STATES PATENTS

| | | | |
|---|---|---|---|
| 2,302,729 | 11/1942 | Whelen................................ | 260/369 |
| 2,435,314 | 2/1948 | Kokatnur............................. | 260/645 |
| 2,435,544 | 2/1948 | Kokatnur............................. | 260/645 |
| 3,766,222 | 10/1973 | Hartwig et al. ...................... | 260/369 |
| 3,786,073 | 1/1974 | Frey et al............................. | 260/369 |
| 3,798,244 | 3/1974 | Mueller et al. ...................... | 260/369 |

FOREIGN PATENTS OR APPLICATIONS
52,206    1/1967    Poland................................ 260/369

OTHER PUBLICATIONS
Reichel et al., as cited in Chemical Abstract 70, 38877z (1969).

Primary Examiner—Lorraine A. Weinberger
Assistant Examiner—Jane S. Myers
Attorney, Agent, or Firm—Plumley and Tyner

[57] ABSTRACT

Process for the preparation of 1-nitroanthraquinone which is practically free of 1,5-dinitroanthraquinone from 1-nitroanthraquinone containing 1,5-dinitroanthraquinone, characterised in that 1-nitroanthraquinone containing 1,5-dinitroanthraquinone is treated with a mixture of concentrated nitric acid and an inert organic solvent, the undissolved constituent is separated off and the 1-nitroanthraquinone is isolated from the solution.

11 Claims, No Drawings

PROCESS FOR THE PREPARATION OF 1-NITRO-ANTHRAQUINONE WHICH IS PRACTICALLY FREE OF 1,5-DINITRO-ANTHRAQUINONE

In the preparation of 1-nitroanthraquinone by nitration of anthraquinone, undesired by-products, especially 2-nitroanthraquinone and 1,5-, 1,6-, 1,7- and 1,8-dinitroanthraquinone, are formed to a considerable extent. At the same time, the nitration product in most cases still contains unchanged anthraquinone.

The known purification processes, for example according to U.S. Pat. No. 2,302,729 or German Offenlegungsschrift (German Published Specification) No. 2,206,960, by heating with aqueous sodium sulphite solution, or according to German Offenlegungsschrift (German Published Specification) No. 2,039,822, by digestion with carboxylic acid amides, relate above all to the removal of the by-products which contain β-nitro groups. However, this process does not permit satisfactory removal of 1,5-dinitroanthraquinone, especially of major amounts of 1,5-dinitroanthraquinone.

The subject of the present invention is now a process for the preparation of 1-nitroanthraquinone which is practically free of 1,5-dinitroanthraquinone, from 1-nitroanthraquinone containing 1,5-dinitroanthraquinone, which is characterised in that crude 1-nitroanthraquinone, containing 1,5-dinitroanthraquinone, such as is obtained, for example, by nitration of anthraquinone, is treated with a mixture of an inert organic solvent and concentrated nitric acid, the insoluble constituent — essentially 1,5-dinitroanthraquinone — is separated off and the 1-nitroanthraquinone, which is practically free of 1,5-dinitroanthraquinone, is again precipitated from the solution — for example by cooling or preferably by eluting the nitric acid — and is isolated.

In the present context, inert organic solvents are to be understood as organic solvents which are miscible with concentrated nitric acid and which under the conditions of the process are largely inert towards the reactants, especially towards concentrated nitric acid.

Examples of solvents which can be used for the process according to the invention are aliphatic and alicyclic hydrocarbons with up to 12, preferably with up to 6, C atoms, which are monosubstituted or polysubstituted by halogen (fluorine, chlorine, bromine or iodine). As examples of such solvents there may be mentioned: methane, ethane, propane, butane, pentane, hexane, cyclopentane and cyclohexane; this list of examples of course includes not only the straight-chain but also the branched isomers, and alkyl-substituted cycloaliphatics.

The chlorine-substituted hydrocarbons should be mentioned as being preferred, for example methylene chloride, chloroform, carbon tetrachloride, 1,1-dichloroethane, 1,2-dichloroethane,, 1,1,2-trichloroethane, 1,1,2,2-tetrachloroethane, pentachloroethane, 1,2dichloropropane and 1,3-dichloropropane, 1,2,3-trichloropropane, 1,1,2,3- and 1,1,3,3-tetrachloropropane, 1,1,1,3,3-pentachloropropane, 1,1,1,2,3,3- and 1,1,1,2,2,3-hexachloropropane, 1,1,1,2,2,3,3- and 1,1,1,2,3,3,3-heptachloropropane and 1,2- and 1,4-dichlorobutane.

Examples of bromine-substituted hydrocarbons which may be mentioned are methylene bromide, bromoform, tetrabromomethane, 1,2-dibromoethane and 1,2-dibromopropane.

Equally, it is possible to use, in the process according to the invention, hydrocarbons which, for example, are substituted by fluorine or are simultaneously substituted by different halogens, for example fluorotrichloromethane, difluorodichloromethane, difluorodibromomethane, 1,1,2-trifluoro-1,2,2-trichloroethane and perfluoro-1,3-dimethylcyclohexane. Of course, mixtures of different organic solvents can also be used.

In the present context, concentrated nitric acid is to be understood as nitric acid containing at least 75% by weight of $HNO_3$, preferably at least 90% by weight of $HNO_3$ and in particular about 98% by weight of $HNO_3$.

The water content of the mixture of solutions is generally so chosen that the ratio of nitric acid to water, expressed in parts by weight, is at least 75 : 25, preferably at least 90 : 10 and in particular about 98 : 2.

The amount and the composition of the solvent mixture can be varied within very wide limits. To avoid losses of 1-nitroanthraquinone, care must be taken, when choosing the solvent mixture, that the $HNO_3$ content in the mixture should be so low, or the water content so high, that nitration of 1-nitroanthraquinone cannot take place at all or can only take place to a limited extent. Whether this is the case can be established by appropriate test experiments in each individual case. For example, in the process according to the invention mixtures containing up to about 30% by volume, preferably up to about 20% by volume, of 98% strength by weight nitric acid can be employed if methylene chloride is used as the organic solvent component. If 1,2-dichloroethane or 1,2-dichloropropane is used as the organic solvent component it is possible to employ, for example, mixtures with up to about 35% by volume, preferably up to about 25% by volume, of 98% strength by weight nitric acid. If the ratio of nitric acid : water is chosen to be less than 98 : 2, larger proportions by volume of the more dilute nitric acids can be used, as compared to the mixtures with 98% strength by weight nitric acid which have been indicated by way of examples.

The amount of the solvent mixture which is used according to the invention is above all determined by the composition of the solvent mixture and generally follows from the solubility of 1-nitroanthraquinone in the particular solvent mixture. As regards the solubility of 1-nitroanthraquinone in the solvent mixture according to the invention it was found, surprisingly, that (1) the solubility of 1-nitroanthraquinone and anthraquinone in the mixture of nitric acid and organic solvent is greater than the sum of the partial solubilities in the individual components of the solvent mixture and (2) the solubility of 1-nitroanthraquinone and anthraquinone, but not that of 1,5-dinitroanthraquinone, increases directly proportionately to the proportion by volume of nitric acid in the solvent mixture, over a certain mixing range of nitric acid and organic solvent. In this mixing range, the molar ratio of the amount of dissolved 1-nitroanthraquinone to the amount of nitric acid required for solution remains constant and is merely dependent on the temperature, the water content and the nature of the organic solvent. For example, at a ratio of nitric acid : water = 98 : 2, the molar ratios nitric acid : dissolved 1-nitroanthraquinone or anthraquinone listed in Table 1 were found. The figures shown in brackets indicate the applicable mixing range, expressed in per cent by volume of 98% strength by weight nitric acid mixed with the organic solvent.

Table 1

| Organic solvent | Molar ratio of HNO₃:1-nitroanthraquinone at 20°C | at 40°C | Molar ratio of HNO₃:anthraquinone at 20°C |
|---|---|---|---|
| Methylene chloride | 4.2 (0–40) | 3.8 (0–40) | 2.9 (0–15) |
| 1,2-Dichloroethane | 5.6 (0–40) | 5.0 (0–40) | 4.8 (0–15) |
| 1,1,2,2-Tetrachloroethane | 3.6 (0–40) | 3.3 (0–20) | 3.7 (0–15) |

In addition to nitric acid, the solution mixture can also contain other mineral acids, which are practically immiscible with the organic solvent, preferably the mineral acids used in the nitration of anthraquinone, for example, sulphuric acid, phosphoric acid or hydrofluoric acid, or strong organic acids such as, for example, alkanesulphonic acids, as well as their acid or neutral salts. The amount in which these additional acids can be present is generally determined by the reaction conditions during the nitration of anthraquinone to crude 1-nitroanthraquinone. The water content of the mineral acid phase should be so chosen that it causes neither undesirable extensive extraction of the nitric acid from the organic solvent nor significant nitration of 1-nitroanthraquinone.

After removing the 1,5-dinitroanthraquinone, the dissolved 1-nitroanthraquinone can be precipitated by cooling the solution, by using up the nitric acid, for example by adding aromatic compounds which can easily be nitrated, for example phenols, naphthols, thiophenols, thionaphthols or their homologues or, particularly advantageously, by eluting the nitric acid from the solvent mixture. Water is preferably used for eluting the nitric acid. However, it is also possible to use compounds having a basic reaction, either in bulk or as a solution, for example in water. Examples of suitable compounds are the alkali metal hydroxides and alkaline earth metal hydroxides such as sodium hydroxide, potassium hydroxide or calcium hydroxide, or their anhydrides, such as calcium oxide, the acid and neutral salts of carbonic acid, especially sodium bicarbonate, sodium carbonate, potassium carbonate, calcium carbonate and barium carbonate, or aliphatic or aromatic amines such as triethylamine, triethanolamine or pyridine. The nitric acid can be eluted completely from the solvent mixture; in order to achieve a special purification effect, especially to remove major amounts of anthraquinone and 2-nitroanthraquinone, it can under certain circumstances be advantageous only partially to elute the nitric acid or consume it by nitration of aromatic compounds which can be nitrated easily, and thereby to keep a major amount of anthraquinone and 2-nitroanthraquinone in solution in the organic mother liquor. Preferably, the nitric acid is eluted completely. In general, the process according to the invention is carried out at temperatures below +70°C, preferably below +50°C and especially approximately at room temperature. The pressure can be varied within wide limits; preferably, the reaction is carried out under normal pressure or under superatmospheric pressure.

The process according to the invention is generally carried out by mixing crude 1-nitroanthraquinone, such as is obtained, for example, by nitration of anthraquinone — preferably without intermediate isolation in the presence of the nitration medium — with the organic solvent, if required adjusting the concentration of the mineral acid to the optimum value and dissolving practically all the 1-nitroanthraquinone by adding concentrated nitric acid. The undissolved 1,5-dinitroanthraquinone and the mineral acid which may originate from the nitration of the anthraquinone are then removed, for example by filtration, decanting and/or centrifuging. If desired, the 1-nitroanthraquinone is precipitated from the solution mixture by cooling or, preferably by eluting the nitric acid with water and/or compounds having a basic reaction. The 1-nitroanthraquinone can then be isolated according to the customary methods, for example by filtration or centrifuging, if appropriate after removing the organic solvent by, for example, distillation or decanting, and can be washed with the organic solvent and/or water and be dried if required.

In a preferred embodiment, anthraquinone is first nitrated in the presence of about 0.2 to about 25, preferably about 0.4 to about 10, and especially about 1, part by volume of an inert organic solvent per part by weight of anthraquinone. Inert organic solvents which are used for this are practically the same solvents as according to the process of the invention, for example halogenated, especially chlorinated, aliphatic and alicyclic hydrocarbons, such as methylene chloride, chloroform, 1,2-dichloroethane, 1,1,2,2-tetrachloroethane or 1,2-dichloropropane. Preferably, the same solvent is employed for the nitration as for the removal of the 1,5-dinitroanthraquinone. The nitrating agent used is generally nitric acid, preferably in combination with other strong mineral acids or Lewis acids such as sulphuric acid, oleum, sulphur trioxide, phosphoric acid, hydrogen fluoride or alkanesulphonic acids, such as methanesulphonic acid, perfluoromethanesulphonic acid, perfluorobutanesulphonic acid or perfluorooctanesulphonic acid. The nitric acid is employed in amounts of up to about 15, preferably about 1–2, mols per mol of anthraquinone and the mineral acid or Lewis acid is employed in amounts of up to about 5, preferably up to about 3 and especially about 1 to 1.5, mols calculated relative to the molar amount of nitric acid.

If required, the concentration of the mineral acid is adjusted to the optimum value after completion of the nitration, and further organic solvent is added. Practically all the 1-nitroanthraquinone is then dissolved by adding concentrated nitric acid, the undissolved 1,5-dinitroanthraquinone and, if relevant, the mineral acid are separated off and the 1-nitroanthraquinone is isolated in the manner described.

The isolated 1-nitroanthraquinone is practically free of 1,5-dinitroanthraquinone, anthraquinone and 2-nitroanthraquinone and can be purified further according to known processes, for example by washing with carboxylic acid amides [compare German Offenlegungsschrift (German Published Specification) No. 2,039,822] or heating with aqueous sodium sulphite solution [compare U.S. Pat. No. 2,302,729 and German Offenlegungsschrift (German Published Specification) No. 2,206,960] or, particularly advantageously, by heating with aqueous sodium sulphite solution in the presence of organic solvents.

According to the latter method, 1-nitroanthraquinone which is practically free of 1,5-dinitroanthraquinone is heated, together with 0.01 – 40, preferably 0.1 – 10, parts by volume of an inert organic solvent, such as, for example, benzene, toluene, xylene, chlorobenzene or chlorotoluene, and an aqueous solution of a salt of sulphurous acid, to temperatures of 75° – 150°C, preferably 80° – 130°C, for several hours. Thereafter the 1-nitroanthraquinone is isolated in the usual manner, if appropriate after removal of the organic solvent, by filtration, decantation or centrifuging and is washed with solvent and/or water. The 1-nitroanthraquinone is then practically free of all by-products and its degree of purity is about 98%.

The process according to the invention can be carried out discontinuously, for example in a stirred kettle, or continuously, for example in a column, circulatory installation, kettle cascade or similar apparatuses.

The process according to the invention offers a series of important advantages over the processes according to the state of the art. Thus 1-nitroanthraquinone which is practically free of 1,5-dinitroanthraquinone and at the same time also free of anthraquinone and 2-nitroanthraquinone can be prepared simply and economically from crude 1-nitroanthraquinone containing 1,5-dinitroanthraquinone. A further particular advantage of the process according to the invention is that the removal of the 1,5-dinitroanthraquinone, anthraquinone and 2-nitroanthraquinone can be carried out in the presence of the nitration medium and hence without intermediate isolation of the crude 1-nitroanthraquinone. Finally, the process according to the invention yields the 1-nitroanthraquinone in a form such that further purification, for example by heating with aqueous sodium sulphite solution, can be carried out particularly simply and effectively.

1-Nitroanthraquinone is an industrial intermediate product which serves, for example, for the manufacture of 1-aminoanthraquinone, an important intermediate product for numerous anthraquinone dyestuffs.

The percentages given in the examples which follow are by weight, unless otherwise stated. Where the strengths of mineral acids are stated in per cent, the remainder is water.

EXAMPLE 1

52 g. of crude 1-nitroanthraquinone containing 86% of 1-nitroanthraquinone, 2% of anthraquinone, 1% of 2-nitroanthraquinone and 5% of 1,5-dinitroanthraquinone (the remainder being 1,6-, 1,7- and 1,8-dinitroanthraquinone) are suspended in 234 ml. of methylene chloride at room temperature, 29.8 ml. of 98% strength nitric acid are added and the mixture is stirred for 15 minutes at room temperature. The undissolved constituent is filtered off and rinsed with 20 ml. of methylene chloride. 250 ml. of water are then stirred into the clear filtrate, the batch is thoroughly mixed for about 1 hour and the precipitate which has separated out is filtered off. It is washed first with about 50 ml. of methylene chloride and then with water until neutral, and is dried. The yield is 40.1 g. The product contains 96% of 1-nitroanthraquinone and less than 0.25% of anthraquinone and 2-nitroanthraquinone and 0.8% of 1,5-dinitroanthraquinone.

EXAMPLE 2

200 g. of crude 1-nitroanthraquinone containing 68% of 1-nitroanthraquinone, 4.5% of anthraquinone, 4.7% of 2-nitroanthraquinone and 6.3% of 1,5-dinitroanthraquinone (the remainder being 1,6-, 1,7- and 1,8-dinitroanthraquinone) are stirred, as in Example 1, with a mixture of 750 ml. of methylene chloride and 95 ml. of 98% strength nitric acid and the mixture is filtered. 900 ml. of methylene chloride are next added to the clear filtrate and 800 ml. of water are then stirred in. The mixture is stirred for a further hour and the precipitate is then filtered off. After washing and drying, 112 g. of 90% pure 1-nitroanthraquinone are obtained, containing 0.5% of anthraquinone, <0.25% of 2-nitroanthraquinone and 1.0% of 1,5-dinitroanthraquinone.

EXAMPLE 3

200 g. of crude 1-nitroanthraquinone containing 82% of 1-nitroanthraquinone, 0.5% of anthraquinone, 0.7% of 2-nitroanthraquinone and 1.9% of 1,5-dinitroanthraquinone are stirred, as in Example 1, with 820 ml. of methylene chloride and 106 ml. of 98% strength nitric acid and the mixture is filtered. 900 ml. of methylene chloride are next added to the clear filtrate, followed by 80 ml. of water, and the mixture is stirred for a further hour. The precipitate is filtered off, washed with about 100 ml. of methylene chloride, then rinsed with water and dried. The yield is 131 g. of 93% strength 1-nitroanthraquinone. The content of anthraquinone and 2-nitroanthraquinone is less than 0.25% and the content of 1,5-dinitroanthraquinone is less than 0.5%. The remainder consists of 1,6-, 1,7- and 1,8-dinitroanthraquinone and can be removed practically completely by heating with aqueous sodium sulphite solution.

EXAMPLE 4

A suspension of 250 g. of anthraquinone in 200 ml. of methylene chloride is treated under reflux conditions, over the course of about 3 hours, with a nitration acid of 68.4 ml. of 98% strength nitric acid and 85.2 ml. of 100% strength sulphuric acid. The mixture is stirred for a further 4 hours at this temperature and cooled to 20°C. After 700 ml. of methylene chloride have been added, 190 ml. of 98% strength nitric acid are allowed to run in at 20°C. After stirring for about 30 minutes longer, the upper, organic phase is withdrawn and clarified by passing it through a frit, and the filter residue is rinsed with a mixture of 95 ml. of methylene chloride and 5 ml. of 98% strength nitric acid. The clear filtrate is decomposed with 500 ml. of water and the mixture is stirred for a further hour at about 20°C. The lemon-yellow precipitate is then filtered off and is washed successively with 2 × 100 ml. of methylene chloride and 2 × 100 ml. of 1% strength aqueous di-sec.-butylnaphthalene-sulphonate solution and finally with water until neutral. After drying at about 100°C, the yield is 229 g. The product contains 89% of 1-nitroanthraquinone and inter alia contains 0.25% of anthraquinone, <0.25% of 2-nitroanthraquinone and 1.4% of 1,5-dinitroanthraquinone. To remove the remaining subsidiary components, the 1-nitroanthraquinone obtained is stirred with 1,850 ml. of 2.5% strength sodium sulphite solution for 4 hours under reflux conditions, then filtered off hot, washed and dried. 204 g. of 1-nitroanthraquinone are obtained, containing 95% of 1-nitroanthraquinone, 0.25% of anthraquinone, <0.25% of 2-nitroanthraquinone and 0.9% of 1,5-dinitroanthraquinone. A further fraction of 12 g. of 1-nitroanthraquinone and 2 g. of anthraquinone remains in the methylene chloride mother liquor and can, after evaporation of the solvent, be reintroduced into the next nitration batch.

EXAMPLE 5

75.9 ml. of 98% strength nitric acid are run into a mixture of 250 g. of anthraquinone and 200 ml. of 1,2-dichloroethane and 94.6 ml. of 100% strength sulphuric acid are then added dropwise at 40°C over the course of about 2.5 hours. The mixture is stirred for a further 4 hours at this temperature and cooled to 20°C. 1,800 ml. of 1,2-dichloroethane and 300 ml. of 98% strength nitric acid are added in succession and the batch is then stirred for 30 minutes at 20°C. After a short settling time, the upper organic phase is withdrawn and clarified by passing it through a frit. The filtrate is decomposed by adding 500 ml. of water whilst cooling, the mixture is thoroughly stirred for a further hour and the precipitate is filtered off at 20°C. The filter residue is washed first with 200 ml. of 1,2-dichloroethane and then with water until neutral, and is dried. The yield is 224 g. Analysis shows that the material contains 86% of 1-nitroanthraquinone, 0.25% of anthraquinone, 0.25% of 2-nitroanthraquinone and 1.8% of 1,5-dinitroanthraquinone. The product is stirred with 66.8 g. of sodium sulphite, 1 g. of di-sec.-butylnaphthalenesulphonate and 1,800 ml. of water for 6 hours at 100°C. 400 ml. of chlorobenzene are then added at about 90°C and the mixture is stirred for a further 4 hours under reflux conditions. It is cooled to 20°C and the precipitate is filtered off and washed first with about 150 ml. of chlorobenzene and then with water. After drying, the yield is 180 g. Determination of the contents of the product shows 98% of 1-nitroanthraquinone, <0.25% of anthraquinone, <0.25% of 2-nitroanthraquinone, 0.6% of 1,5-, 0.3% of 1,6-, 0.3% of 1,7- and 0.3% of 1,8-dinitroanthraquinone. A further fraction of 20 g. of 1-nitroanthraquinone and 2 g. of anthraquinone remains in the 1,2-dichloroethane mother liquor whilst 4 g. of 1-nitroanthraquinone and 0.5 g. of anthraquinone remain in the chlorobenzene mother liquor and can, after evaporation of the solvent, be reintroduced into the next nitration batch. The total yield is then 67% of theory.

EXAMPLE 6

200 g. of crude 1-nitroanthraquinone containing 82% of 1-nitroanthraquinone, 0.5% of anthraquinone, 0.7% of 2-nitroanthraquinone and 1.9% of 1,5-dinitroanthraquinone are stirred, as in Example 1, with 850 ml. of methylene chloride and 110 ml. of 98% strength nitric acid, and filtered. 2 l. of water are added to the clear filtrate, with vigorous stirring, and the methylene chloride is distilled off. The aqueous suspension is filtered hot and the precipitate is washed with water, until neutral, and dried. The yield is 179 g. of 85% strength 1-nitroanthraquinone containing 0.5% of anthraquinone, 0.7% of 2-nitroanthraquinone and <0.5% of 1,5-dinitroanthraquinone.

I claim:

1. In a known process for the purification of 1-nitroanthraquinone by isolating 1-nitro-anthraquinone from an impure composition containing anthraquinone nitration products and reactants primarily containing 1-nitro-anthraquinone and containing as an impurity 1,5-dinitro-anthraquinone, the improvement comprising removing 1,5-dinitro-anthraquinone by adding to said composition a mixture of concentrated nitric acid, containing at least 75% by weight $HNO_3$ and not more than 25% by weight $H_2O$ and an inert organic solvent which is miscible with the concentrated nitric acid and is selected from the group consisting of aliphatic and alicyclic hydrocarbons with up to 12 carbon atoms, and halogen derivatives thereof, wherein the relative quantities of nitric acid and inert organic solvent in said mixture as well as the total quantities in said composition, are such that the solubility of 1-nitroanthraquinone and anthraquinone in the mixture of nitric acid and organic solvent is greater that the sum of the partial solubilities in the individual components of the solvent mixture and subsequently, the undissolved 1,5-dinitroanthraquinone containing constitutent is separated from the solution thus formed.

2. Process according to claim 1, characterised in that the ratio of nitric acid:water in the mixture is at least 90:10.

3. Process according to claim 2 wherein the ratio of nitric acid:water in the mixture is at least about 98:2.

4. Process according to claim 1, characterised in that at nitric acid:water ratios of about 98:2 the maximum volume ratio of nitric acid:inert organic solvent is 35:65.

5. Process according to claim 1, characterised in that nitration mixtures obtained on nitrating anthraquinone are employed as said composition without intermediate isolation of the crude 1-nitroanthraquinone.

6. Process according to claim 5, characterised in that the anthraquinone has been nitrated in the presence of organic solvents.

7. Process according to claim 1, characterised in that the 1-nitroanthraquinone is isolated by precipitation from the remaining solution by adding water.

8. Process according to claim 1, characterised in that halogenated, aliphatic or alicyclic hydrocarbons are used as inert organic solvents.

9. Process according to claim 8 wherein said halogen is chlorine.

10. Process according to claim 1, characterised in that methylene chloride and/or 1,2-dichloroethane and/or 1,2-dichloropropane are used as the organic solvent.

11. Process according to claim 1, in that the isolated 1-nitroanthraquinone in the presence of organic solvents, is heated with aqueous sodium sulphite solution.

* * * * *